United States Patent [19]

Forrest et al.

[11] Patent Number: 5,580,524
[45] Date of Patent: Dec. 3, 1996

[54] ASSAY OR REACTION APPARATUS WITH AGITATING DEVICE

[75] Inventors: Gordon C. Forrest, East Horsley; Mervyn N. Sennett, Fleet; John Curtis, Ashford, all of United Kingdom

[73] Assignees: Anagen Limited, Hampshire; Wilj International Ltd., Kent, both of Great Britain

[21] Appl. No.: 335,197

[22] Filed: Nov. 7, 1994

Related U.S. Application Data

[63] Continuation of Ser. No. 125,285, Sep. 22, 1993, abandoned, which is a continuation of Ser. No. 34,233, Mar. 22, 1993, abandoned, which is a continuation of Ser. No. 947,499, Sep. 18, 1992, abandoned, which is a continuation of Ser. No. 853,548, Mar. 18, 1992, abandoned, which is a continuation of Ser. No. 762,869, Sep. 18, 1991, abandoned.

[30] Foreign Application Priority Data

Sep. 18, 1990 [GB] United Kingdom .................. 9020352

[51] Int. Cl.⁶ .................................................. G01N 35/02
[52] U.S. Cl. .......................... 422/63; 422/64; 422/65; 422/67; 422/100; 422/104; 436/43; 436/47; 436/48; 436/49; 436/174; 436/180; 366/213
[58] Field of Search .................. 422/63–67, 68.1, 422/100, 104; 436/43, 47, 48, 49, 54, 174, 179, 180, 808; 366/208, 209, 213, 214, 217, 218

[56] References Cited

U.S. PATENT DOCUMENTS

| | | | |
|---|---|---|---|
| 3,115,966 | 12/1963 | Leifer | 422/64 |
| 3,322,958 | 5/1967 | Heiss | 422/64 |
| 3,432,049 | 3/1969 | Howells | 422/64 |
| 4,058,367 | 11/1977 | Gilford | 422/65 |
| 4,479,720 | 10/1984 | Mochida et al. | 366/214 |
| 4,518,264 | 5/1985 | Nohso | 366/208 |
| 4,582,990 | 4/1986 | Stevens | 250/328 |
| 4,678,752 | 7/1987 | Thorne et al. | 435/291 |
| 4,788,150 | 11/1988 | Nelson et al. | 436/45 |
| 4,835,707 | 5/1989 | Amano et al. | 364/497 |
| 5,051,238 | 9/1991 | Umetsu et al. | 422/64 |
| 5,055,408 | 10/1991 | Higo et al. | 436/48 |
| 5,075,079 | 12/1991 | Kerr et al. | 422/64 |
| 5,104,808 | 4/1992 | Laska et al. | 436/48 |
| 5,122,342 | 6/1992 | McCulloch et al. | 422/65 |
| 5,158,895 | 10/1992 | Ashibara et al. | 436/526 |
| 5,175,086 | 12/1992 | Takekawa et al. | 435/7.92 |
| 5,176,880 | 1/1993 | Iwasaki et al. | 422/63 |
| 5,183,638 | 2/1993 | Wakatake | 422/64 |
| 5,202,091 | 4/1993 | Lisenbee | 422/52 |
| 5,215,714 | 6/1993 | Okada et al. | 422/64 |
| 5,272,092 | 12/1993 | Hamasaki et al. | 436/172 |

FOREIGN PATENT DOCUMENTS

| | | |
|---|---|---|
| 0013452 | 7/1980 | European Pat. Off. . |
| 0410645 | 1/1991 | European Pat. Off. . |

*Primary Examiner*—Long V. Le
*Attorney, Agent, or Firm*—Hamilton, Brook, Smith & Reynolds, P.C.

[57] ABSTRACT

The invention provides an assay or reaction apparatus of modular construction permitting true random operation at the discretion of the user. The apparatus is an automated multi-test capability assay or reaction apparatus (1) in modular form, comprising a reagent and an assay sample storage module (2,3), an incubation module (11), a reaction detection/measurement module (17), and a module (16) for independently and, as desired, both transporting an incubation container (58) between the incubation module (11) and reaction detection/measurement module (17), and transferring reagent(s) and/or assay sample(s) between different modules without reagent(s) and/or assay sample(s) intended for different tests or reactions.

5 Claims, 10 Drawing Sheets

ASSAY OR REACTION APPARATUS WITH AGITATING DEVICE

Related Applications

This is a Continuation application of U.S. patent application Ser. No. 08/125,285, filed on Sep. 22, 1993, now abandoned, which is a Continuation of U.S. patent application Ser. No. 08/034,233, filed on Mar. 22, 1993, now abandoned which is a Continuation of U.S. patent application Ser. No. 07/947,499, filed on Sep. 18, 1992, now abandoned, which is a Continuation of U.S. patent application Ser. No. 07/853,548, filed on Mar. 18, 1992, now abandoned, which is a Continuation of U.S. patent application Ser. No. 07/762,869, filed on Sep. 18, 1991, now abandoned.

BACKGROUND OF THE INVENTION

Automated analytical instrumentation for the imunochemical testing of samples is well known. Typically, a sample of fluid such as human serum, plasma, CSF or urine is combined with one or more prepared liquid reagents and after appropriate specific time periods have elapsed and further reagents added if necessary, one or more characteristics of the mixture is observed to provide an analytical result. Automation of these tests confers advantages over the manual procedures which a laboratory technician has to follow, such as improved accuracy and precision of control of timings, volumes of fluids, and temperatures, leading to improvements in accuracy and repeatability of the testing. In addition, automation of testing can provide results more rapidly and more cost-effectively than manual testing.

Automated clinical analyzers generally provide a means of transporting the reaction mixtures of different test samples between the various operating stations needed to perform the tests. Thus the mixtures are moved between positions at which reagent addition, removal, mixing, washing, incubation and detection are performed, the precise timing and sequence being a function of the type of technology being used to conduct the assay. One such analyzer, the IMx, is sold by Abbott Laboratories. A weakness of this instrument is that the sequence of movement and timing at each station is the same for all samples being analyzed, and once started, each test progresses in sequence through the system. This, combined with the limitation of having reagents stored on the instrument for only one type of analysis, restricts its application to running pre-defined batches of samples, with no flexibility for performing different analyses on the same sample.

Other instruments, such as the SR1 sold by Serono Diagnostics and the Affinity sold by Becton Dickinson (EP-A-223 002) avoid some of these limitations by providing the test specific reagents in a unit-dose pack which incorporates chambers both for storage of the reagents and for performing the test. Such systems permit the individual reaction mixtures to access the various workstations at time intervals which are independent of each other, and can thus process different kinds of tests in any order.

A major disadvantage of these random access systems is the requirement to have individually packaged test specific reagents for each analysis to be performed. Typical unit-dose reagent packs have up to 4 separate reagents provided therewithin, and while seeming convenient for the user, this is a very costly way of providing the reagents due to high packaging costs, excessive volumes of fluids being provided in order to guarantee sufficient for running the test, and relatively high costs of providing refrigerated storage space due to the bulky nature of the packs. Manufacturing and quality control of such packs is necessarily complex, batch homogeneity being difficult to establish and scrap rates can be high.

A feature of these systems is the positioning of the sample/reagent reaction mixture around the periphery of a rotatable carousel, this being the means of transporting the mixtures to the various operating stations. Movement of one mixture to a particular station then displaces all other mixtures at the same time; movement which can then expose them to varying temperatures and other disturbances. Thus, although they are called random access analyzers, processing of each sample is not truly independent of all others. Also, scheduling of tests can become restricted if every one of the test mixtures is moved for each operation of each sample.

It is one objective of the present invention to overcome disadvantages of the above described systems by providing the test specific reagents for a variety of different tests stored in an apparatus unit bulk form, and configuring the sample/reagent reaction mixture transport system such that a chosen material can be accessed for processing in a manner which does not influence the others in any way. Bulk storage of reagents on the instrument not only improves reagent manufacturing efficiency and economics, but allows more reliable storage since the temperature can be controlled on the instrument. By dispensing with the need for unit-dose packs, improved convenience of sample loading can be accommodated by designing the instrument to accept the primary draw tubes, which can be sampled for a variety of different tests to be performed.

SUMMARY OF THE INVENTION

This invention relates to an assay or reaction apparatus. The principles of the present invention are of broad applicability, but the invention is particularly described with reference to immunoassay apparatus systems, specifically automated immunoassay apparatus. This invention particularly relates to a modular form assay or reaction apparatus in which transport and/or thermal control is such as to permit true random operation at the discretion of the user. It will be appreciated that the individual modular constructions of the present invention, and the principles revealed thereby, are not restricted to immunoassay applications, but are of general applicability to systems where careful reaction control in a number of respects is important.

In general, and without implying limitation of the subject matter which makes up the present inventive concept solely to what immediately follows, important inventive aspects now provided include:

(a) A modular form assay or reaction apparatus configured as a unit and equipped to be capable of effecting a plurality of tests or reactions, comprising means for the storage of sample(s), means for the storage of bulk quantities of reactant(s), means for taking from bulk quantity and dispensing unit quantities of reactant(s), means for the transport of reactant(s) and/or sample(s), and means for the performance of individual reactions or tests selected on a random basis without interference with other reactions or tests which the apparatus is capable of performing.

(b) A transport mechanism for use in a single unit multi-reaction apparatus or multi-test assay apparatus having a plurality of work stations, comprising a gantry on which is mounted means for carrying fluids and means for carrying a selected container from one work station to another within the unit, both of which means are independently movable backwards and forwards along the gantry and are capable of independently moving their respective loads in at least some directions normal thereto.

(c) An automated multi-test capability assay apparatus in modular form, comprising a reagent and/or assay sample storage module, an incubation module, a reaction detection/measurement module, and means for independently and, as desired, both transporting an incubation container between the incubation module and reaction detection/measurement module, and transferring reagent(s) and/or assay sample(s) between different modules without moving reagent(s) and or assay sample(s) intended for different tests.

(d) A put-down/pick-up apparatus for reaction/assay vessels comprising elastic means, for example a spring, means for adjusting the tension of the elastic means and a plurality of fingers held by the elastic means and which can be positionally adjusted by adjustable biasing between a position permitting gripping of the vessel therebetween and an open non-gripping position by adjustment of the tension adjustment means to compress the elastic means.

(e) An apparatus for ensuring solid phase suspension in an assay or reaction system, comprising a rotatable support having means for independently rotatably mounting a vessel containing assay or reaction components, a drive wheel adapted to rotate such vessel when present in its mounting, and a driving surface of greater circumferential dimension than the drive wheel and surrounding the drive wheel and engageable therewith such that upon rotation of the rotatable support the drive wheel is rotated around the driving surface and the vessel thus rotated at a rate exceeding the rate of rotation of the rotatable support.

(f) A carousel arrangement for an assay or reaction apparatus, comprising concentrically arranged and independently rotatable carousels with at least one inner carousel thermally insulated from an outer carousel, at least one of the carousels preferably being maintained at a controlled sub-ambient temperature.

(g) A modular-form assay or reaction apparatus configured as a unit and equipped to be capable of effecting a plurality of tests or reactions, comprising an optional sample load/unload module (present in the case of an assay apparatus), a sample and/or reagent storage module, a reaction incubation module, an optional substrate and wash module for separation and washing of solid phase, an optional detection/reader module for reaction detection and/or measurement, and a transport module for transporting an assay or reaction vessel between modules, wherein each of the modules, optionally with the exception of the sample load/unload module (if present), is equipped with temperature control means to permit independent temperature control of modules in the apparatus.

(h) An automated immunoassay apparatus individual module of work station substantially as hereinafter described with reference to and as illustrated in any one or more of the accompanying drawings if and as appropriate.

(i) An optionally temperature controlled optical reaction detection or reading system, comprising means for holding a cuvette containing liquid, a source of a predetermined defined beam of electromagnetic radiation orientated to pass the beam through the cuvette, means for assessing a resultant beam after such passage, and magnet means for attracting magnetizable solid phase particles in the cuvette away from the path of the beam.

(j) An optionally temperature controlled optical reaction detection or reading system, comprising means for holding a cuvette containing liquid, means for measuring electromagnetic radiation emitted from the liquid resulting from either passing a predetermined defined beam of electromagnetic radiation into the liquid or from addition of reagent capable of causing emission of chemiluminescent light from components of the liquid, and magnet means for attracting magnetizable solid phase particles in the cuvette away from the path of the emitted electromagnetic radiation.

(k) A cuvette suitable for optical reading of the contents thereof and comprising a first portion for optical reading having at least one substantially planar surface for entry of a beam of electromagnetic radiation and at least one substantially planar surface for exit of a beam of electromagnetic radiation, and a second portion carrying positioning means allowing for precise orientation of the cuvette in a receiver adapted therefor, optionally the positioning means comprises positioning projections.

In preferred aspects, the present invention provides a system for performing completely automated immunoassays which overcomes difficulties associated with previous systems. The system preferably comprises a stand-alone unit which incorporates means for sample and reagent storage, means for picking-up, transferring and dispensing fluids, transport means, incubation means, measuring means, washing means, and data reduction means.

Such a system is particularly suited to the automation of immunoassays which are based on the use of antibody—or antigen—coated magnetizable particles as a solid-phase for separation of free and bound fractions. The system can be configured for all known signal systems (colorimetric, enzyme, fluorescence, luminescence, etc.) but in particularly preferred embodiments an enzyme tag is utilized to generate a signal. A substrate may be used which, in conjunction with the enzyme, generates a fluorescent product as a signal. A chemiluminescent signal system may also be used, in which case a developer solution may be added to cause emission of chemiluminescent energy from the contents of the assay mixture.

The present inventive concept, and its associated inventive aspects and inventions will now be described with reference to the accompanying drawings. The following description consists of three sections. In the first section, an overall general structural description is given. In the second section, a description is given of a performance of an assay in general terms. In the third section, more detailed description is given with reference to particular figures, showing the fine construction of various modules which are part of the inventive concept. The third section also incorporates guidance regarding system electronics and software for computer control of the apparatus but it will be appreciated that the design and performance as such can be a matter of user choice and customized design, and the reader of skill in electronic/computer control of automated immunoassay apparatus will have no difficulty in realizing how such an apparatus can be controlled.

DETAILED DESCRIPTION OF THE INVENTION

Figure 10:
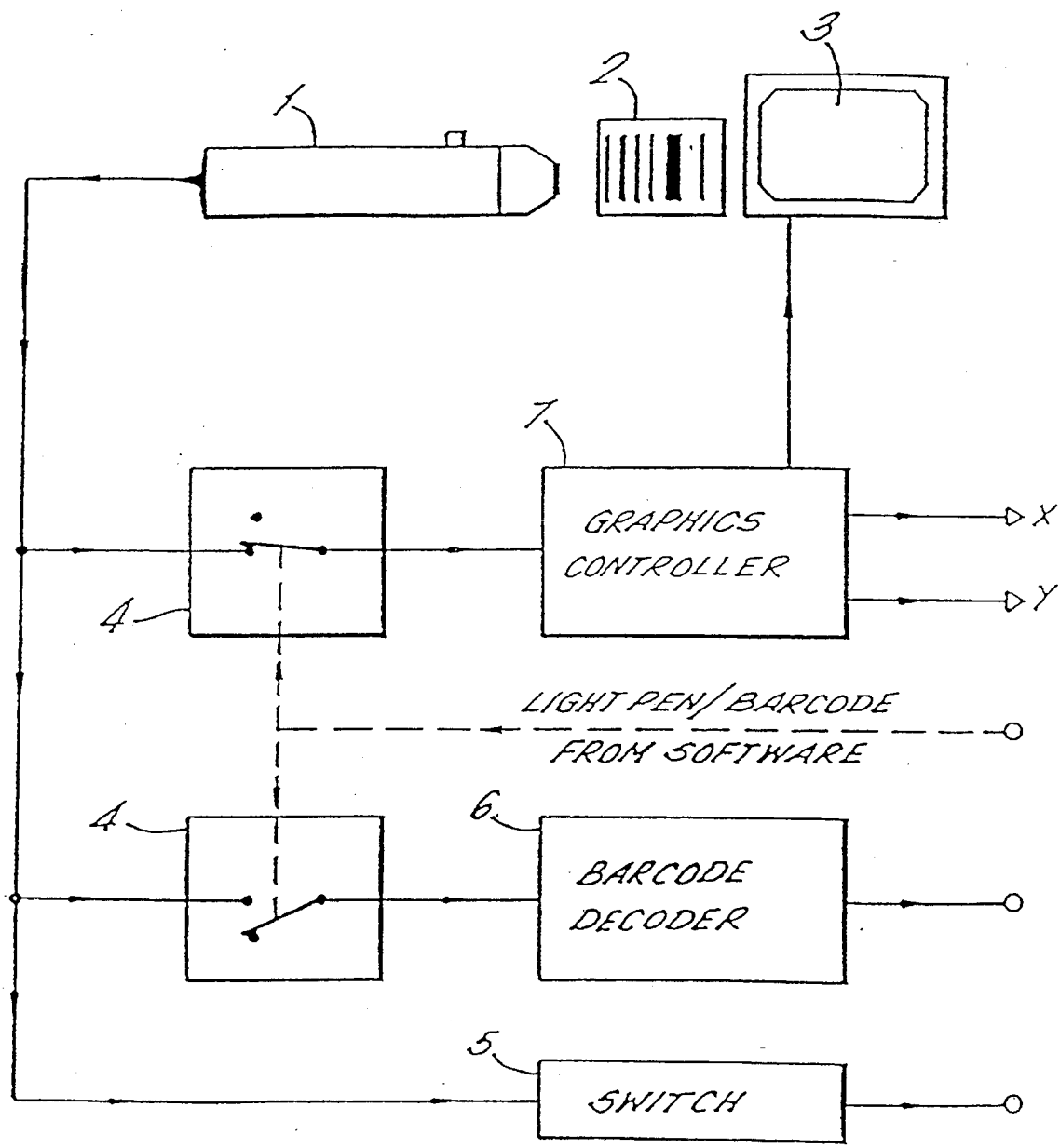
FIG. 10 illustrates a combined bar-code reader and light pen system for use in the present inventive concept.

Referring now generally to all of the Figures of the drawings except for FIG. 10 thereof, the invention employs a reaction cuvette (58) which performs the function of a vessel in which the reactions take place and a vessel where measurement of the signal is made. Although not illustrated in such form, the curvette (58) can be of the type which carries on its internal surface or an extension thereof or on a specially provided spindle an immobilized reagent. If this type of cuvette is employed, such immobilization can be achieved by any means known in the art.

The system is configured around a series of modules for performing the various steps necessary to perform the analyses, and these are contained in an outer case (1). The modules are linked by a variety of transport means for transferring liquids and cuvettes between the modules. The details and layout of the modules could be adapted to suit particular needs, but in a preferred embodiment for performing fluorescent enzyme immunoassays utilizing magnetizable particles they comprise the following:

A sample carousel (2) which contains tangential slots (7) for retaining a multiple of sample tube racks (6). In a preferred embodiment there is provision for 20 racks on the sample carousel and each rack has holes for 4 sample tubes of size 8–18 mm diameter and 50–100 mm long. The carousel can rotate in both clockwise and anti-clockwise directions in a controlled manner.

A sample load/unload station (4) which can accommodate a single sample tube rack (6) and where sample tubes can be loaded or unloaded into the sample tube rack (6). In addition, the sample load/unload station (4) contains a means for transporting sample tube racks onto and off of the sample carousel (2).

A reagent carousel (3) which contains multiple locations (9) for multi-chambered reagent packs (8) containing bulk assay specific reagents for performing multiple tests of a particular assay. In a preferred embodiment there are locations for 20 reagent packs and each reagent pack contains sufficient reagents for 100–200 determinations, depending on assay type. The reagent carousel (3) contains cooling means for maintaining the temperature of the stored reagents at 2°–8° so that they may remain on the instrument for protracted periods. Although concentric with the sample carousel (2), the reagent carousel (3) can rotate independently of it and both can rotate in clockwise and anti-clockwise directions in a controlled manner.

An incubation tray (11) which contains multiple locations for reaction curvette trays (12). Each reaction cuvette tray contains a multiple of locations (14) for holding reaction cuvettes (58). In a preferred embodiment of the invention, the incubation tray (11) can accommodate 4 reaction cuvette trays (14), and each reaction cuvette tray can accommodate 56 reaction cuvettes (58). The incubation tray (11) is capable of orbital rotation, to mix liquids in the reaction cuvettes (58), and move linearly in a controlled manner in the Y axis. The incubation tray (11) contains means to maintain a controlled temperature of the tray itself and the contents, and is enclosed by an insulated chamber (not shown). In a preferred embodiment of the present invention, the temperature is maintained at 37° C.±1° C.

The substrate and wash station (15) comprises a rotatable central carousel and a multiple of units distributed evenly around the circumference for washing the solid-phase particles or addition of the substrate. The central carousel contains a multiple of holes (50) for holding cuvettes (58). In a preferred embodiment of the invention there are 4 holes (50), two wash units and one substrate addition unit. Each unit comprises a permanent magnet, to attract the particles to a particular region of the cuvette (58), an aspiration probe (21) and either a dispense probe for wash buffer (22) or substrate (23) as appropriate.

The substrate and wash station (15) contains means for maintaining the temperature of the station at a constant temperature, and for ensuring that all fluids are dispensed at a constant temperature. The SAW station (15) is enclosed in an insulated chamber (not shown). In a preferred embodiment of the invention, the substrate and wash station is maintained at a temperature of 37° C.±1° C., wash buffer is dispensed at 37° C.±2° and substrate at 37° C.±0.2° C. The substrate and wash station contains means for resuspending the magnetizable particles after addition of fluid.

The detection/reader station (17) contains a chamber (32) for holding the cuvette (58) for measurement of the end-point signal of the reaction. In a preferred embodiment of the invention, the reader station is a fluorimeter, and encompasses probes for addition of stop solution (24) and aspiration of contents (25). When a chemiluminescent signal system is used, probe (24) may alternatively be used for the addition of reagent designed to cause emission of chemiluminescent energy from the contents of the assay mixture, e.g. luminol with a peracid salt.

The detection/reader station is contained within an insulated chamber (not shown) and includes means to maintain the temperature of the station, its contents and dispensed fluids at a constant temperature. In a preferred embodiment of the invention the temperature of the station and content is maintained at 37° C.±1° C., the stop fluid is dispensed at 37° C.±1° C.

A transport mechanism (16) which runs above the other modules and carries the sample/reagent pipette mechanism

(18) and the cuvette transport mechanism (20). These can move independently in a controlled manner along gantry (10) in a x-axis, and encompass means whereby the operational part of each can move independently in the y-axis. Thus by independent rotation of mechanisms (2), (3), and (15), and movement of mechanism (11) in a z-axis, mechanisms (18) and (20) can access vessels (8), and cuvettes (58) when held in locations (14) and (50).

Sample/reagent pipette mechanism (18) encompasses a probe or probes and a pump means whereby samples of assay-specific reagents can be dispensed in predetermined quantities, and a washing means (19) to minimize cross-contamination of fluids.

The cuvette transport mechanism (20) contains a grabber whereby reaction cuvettes (58) can be securely grabbed and placed to facilitate their transfer from module to module as required.

In addition, the invention includes containers for bulk common reagents, together with dispensing means to facilitate addition of fluids to the reaction cuvettes as appropriate. In a preferred embodiment of the invention this includes a substrate bottle (33) and dispensing pump (34) which is connected to wash probes (22) and probe wash mechanism (19) by tubing (not shown), a stop solution bottle (35) and dispensing pump (36) connected to the stop dispense probe (24) by tubing (not shown).

Waste fluids from the aspiration probes (21) and (25), and from the sample/reagent pipettor probe wash means (19) are transferred to a waste container (39) by pump means (40).

The electronics are contained in a sealed compartment (27) and can include power supply units, computers, disc drives etc which control instrument functions, assay data reduction and data storage.

All liquid containers [assay specific reagent pack (8), wash buffer container (37), stop buffer container (35) and substrate container (33)] are disposable items. Each is labelled in a machine-readable form with information on component, expiry date, batch number etc which is entered into the instrument memory on loading the containers onto the instrument. In the case of the specific reagent pack (8) additional information encoded includes details of dose-response relationship, calibrator limits etc. In a preferred embodiment of the invention, this information is in the form of a bar-code which may be entered into the instrument memory via a combined light pen/bar code reader. Means may also be provided for accounting for volumes of the various reagents resident on the instrument.

A suitable light pen/barcode reader for the above purpose is shown in FIG. 10. In FIG. 10, separate reference numerals 1 to 7, inclusive, are used which do not correspond to similarly numbered reference numerals in other Figures of the drawings. The combined pen/reader (1) is configured as a hand held pen or wand and is energized by switch (5) and contains an optical sensor (not shown) which is sensitive to both infra-red light signals reflected from a bar code label (2) and light signals emitted from a visual display unit (3) of the apparatus of this invention. Bar code label (2) may be, for example, on a patient sample and thus supply identifying and other patient data, or may be, for example, on a source of reagent or a unified test pack including materials necessary for a particular desired test and thus supply test-related information. Signals picked up by combination 1 are separated by means of a software controlled "switch" system (4) which has pre-programmed system knowledge of whether a bar code or a VDU screen cursor position is being read. Once the signals have been correctly directed, any bar code data stream is decoded via a micro-controller (6) which can be constructed in a manner known in the art, and any visual display unit raster scan pulse is decoded into a screen X-Y address by a graphics AT controller (7), which controller (7) can again be of conventional construction. The pen/reader thus enables an operator to use a single hand-held device to perform two separate operations, each of which would normally require different manipulative steps.

The user interface can thus comprise the aforesaid VDU, a keyboard, a printer and a combined bar-code reader/light pen as described. Bidirectional communication with host or satellite communication is provided by an RS232 port in the electronics pack (27), and data may be inputted or outputted via a floppy or disc drive. The skilled reader will appreciate how machine control can be organized.

Turning now to use of the system, and referring mainly to FIGS. 1 to 9 of the drawings, to perform an assay, a sample identifier is entered into the instrument memory either from bar-code on the sample tube via a combined bar code reader/light pen or through the keyboard. The sample is then placed into the appropriate hole (13) in a sample tube rack (6) positioned in the load/unload station (4). The hole in which the tube is inserted may be marked by an LED adjacent to the appropriate hole, and correct insertion confirmed by a detector in the load/unload station (4).

The assays to be performed on the sample by the instrument are then selected from the VDU screen which displays a menu of the assay specific reagent packs resident on the instrument. Selection can be made using a light pen/bar-code reader (see before). When the sample tube rack (6) is filled (or partly filled if desired), the load/unload station means (4) transfer the sample tube rack (6) onto a vacant slot (7) on the sample carousel (2). An empty sample tube rack is then presented at the load/unload station (4) for further patient samples. The process is repeated until all positions are full or the supply of samples is exhausted. Performance of the assays can start immediately after samples are on the sample carousel (2), and when a rack of samples has been sampled for assay, the sample tube rack (6) can be returned to the load/unload station for replacement with different samples. Addition of further samples for assay can be carried out at any time during instrument operation that vacancies are available on the sample carousel.

Performance of the assay may be entirely automatic by the instrument under control of an in-built computer.

Aliquots of sample and specific reagents are transferred from the sample tube and assay-specific reagent packs (8) by the sample/reagent pipette (18) to a reaction cuvette (58) located in a tray (12) in the incubation tray (11). Between aliquots of fluid the probes are cleaned by the probe wash means (19) to reduce contamination. After an incubation period the reaction cuvette (58) is transferred to the substrate and wash station (15) by the cuvette transport means (20) for washing of the magnetizable particle solid-phase to remove unbound material and addition of substrate. The cuvette is then returned to the cuvette tray (12) in the incubation tray (11). After a period of incubation, the reaction cuvette (58) is transferred to the reader station (17) by the cuvette transport means (20) for addition of stop solution via probe (24) and the signal measured. The contents are then aspirated via aspiration probe (25) and the empty cuvette returned to the cuvette tray (12).

When all the reaction cuvettes (58) in a tray (12) have been used, the tray and cuvettes can be removed and disposed of and then replaced with a fresh cuvette tray (12) containing unused cuvettes (58). The signal from the fluorescence is transmitted to an in-built computer, and the dose of unknown sample calculated from a stored dose-response curve. Details of the batch-specific dose response curve for each assay may be encoded in machine-readable form on the specific reagent packs (8) and entered into the instrument memory via a combined light pen/bar code reader.

Because of the independent nature of the modules and the independent nature of the sample/reagent pipette mechanism (18) and cuvette transport mechanism (20), virtually any variation of protocol (in terns of order of addition of reagents, delayed addition of reagent, immunoincubation times, substrate incubation times, number of wash cycles, etc.) is possible. Specific, optimized protocols can be accommodated which may be entered into the instrument via floppy discs.

In preferred embodiments of the invention for 2-site immunometric assays for antigens, the protocols are of the forward sequential immuno-incubation type, i.e., sample is contacted with solid-phase antibody specific to the analyte to be measured and after an initial incubation a second analyte-specific antibody labelled with a signal moiety is added to the incubation mixture and a further period of incubation allowed prior to separation of bound and unbound fractions. In particularly preferred embodiments the solid-phase antibody is a polyclonal antibody and the labelled antibody is a monoclonal antibody.

In what follows, more detailed description will be given, with reference to the drawings, in order to permit greater understanding of the overall structure of an immunoassay apparatus in accordance with the present invention, and the structure of individual modules. It should be clearly understood that the ambit of the present inventive concept is such that it includes not only novel modules or modules having similar structure (the skilled man will readily appreciate ways in which the modules of the present invention may be varied to suit requirements), but also the use of such modules, individually or in combination, in reaction apparatus or other assay apparatus. Furthermore, the present inventive concept embraces parts and sections of such modules which are themselves new. It will thus be appreciated that the inventive concept disclosed herein addresses not merely a unit machine in modular form concept, but also the parts and sections thereof which go to make up the overall apparatus.

In what follows, particular modules/sections of the illustrated apparatus will be considered individually and thereafter some guidance will be given to electronics and software control.

Figure 1:
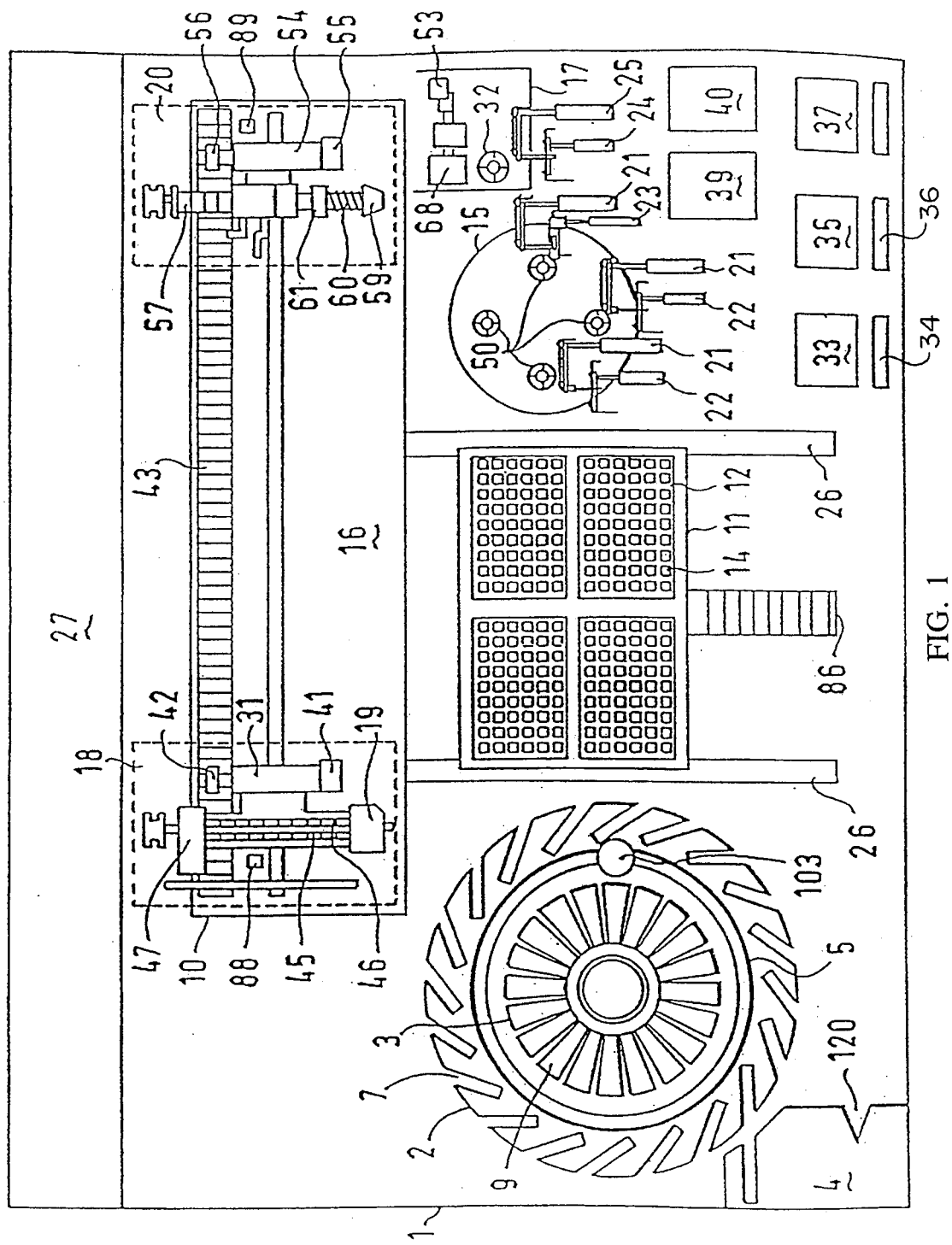
FIG. 1 is an overall schematic view of a unit apparatus for immunoassay purpose which is in modular form and is in accordance with the present inventive concept.
Figure 2:
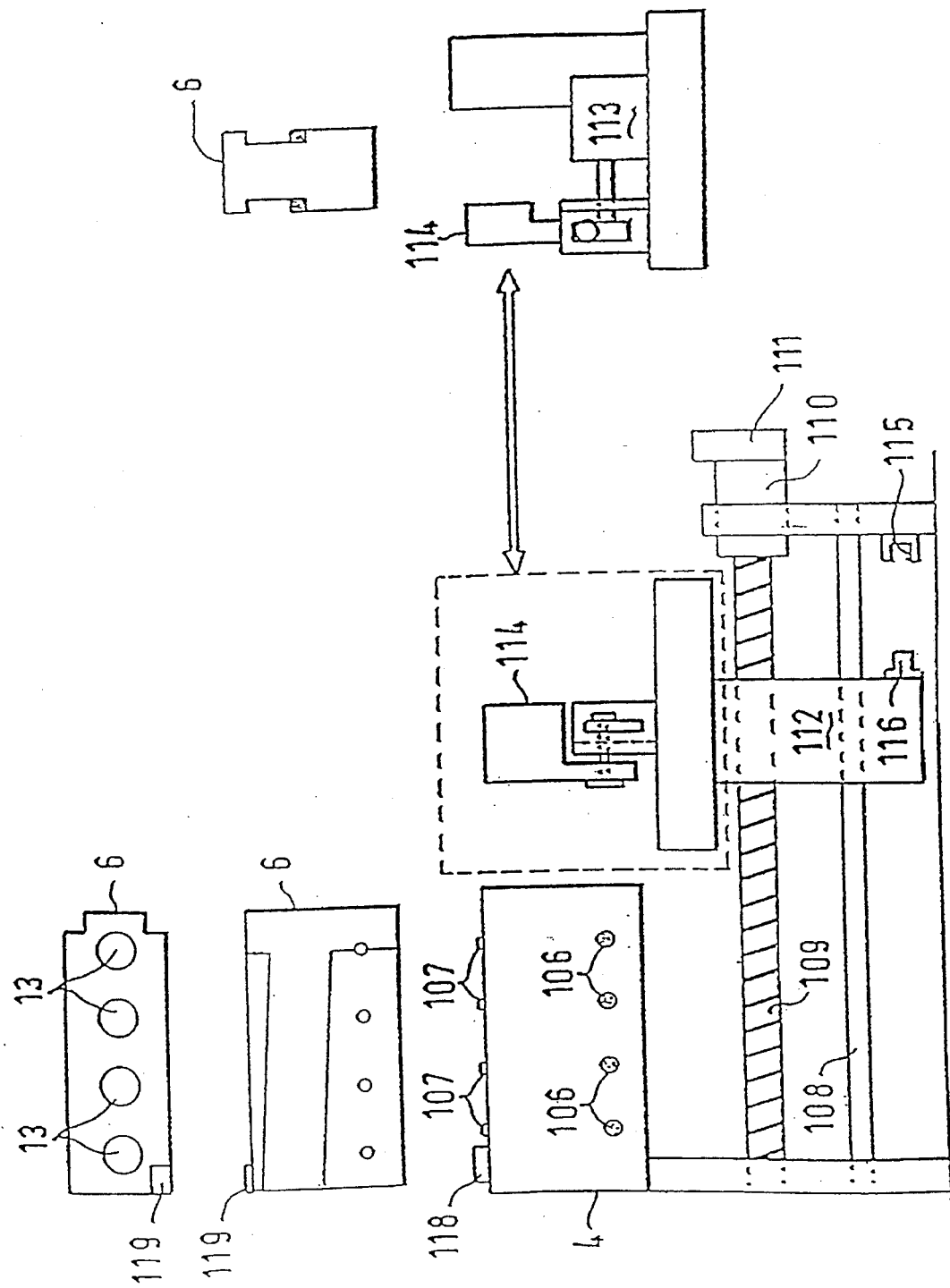
FIG. 2 shows view of a sample load/unload module in accordance with the present inventive concept, and also shows views of typical sample tube racks usable in such a module.
Figure 3:
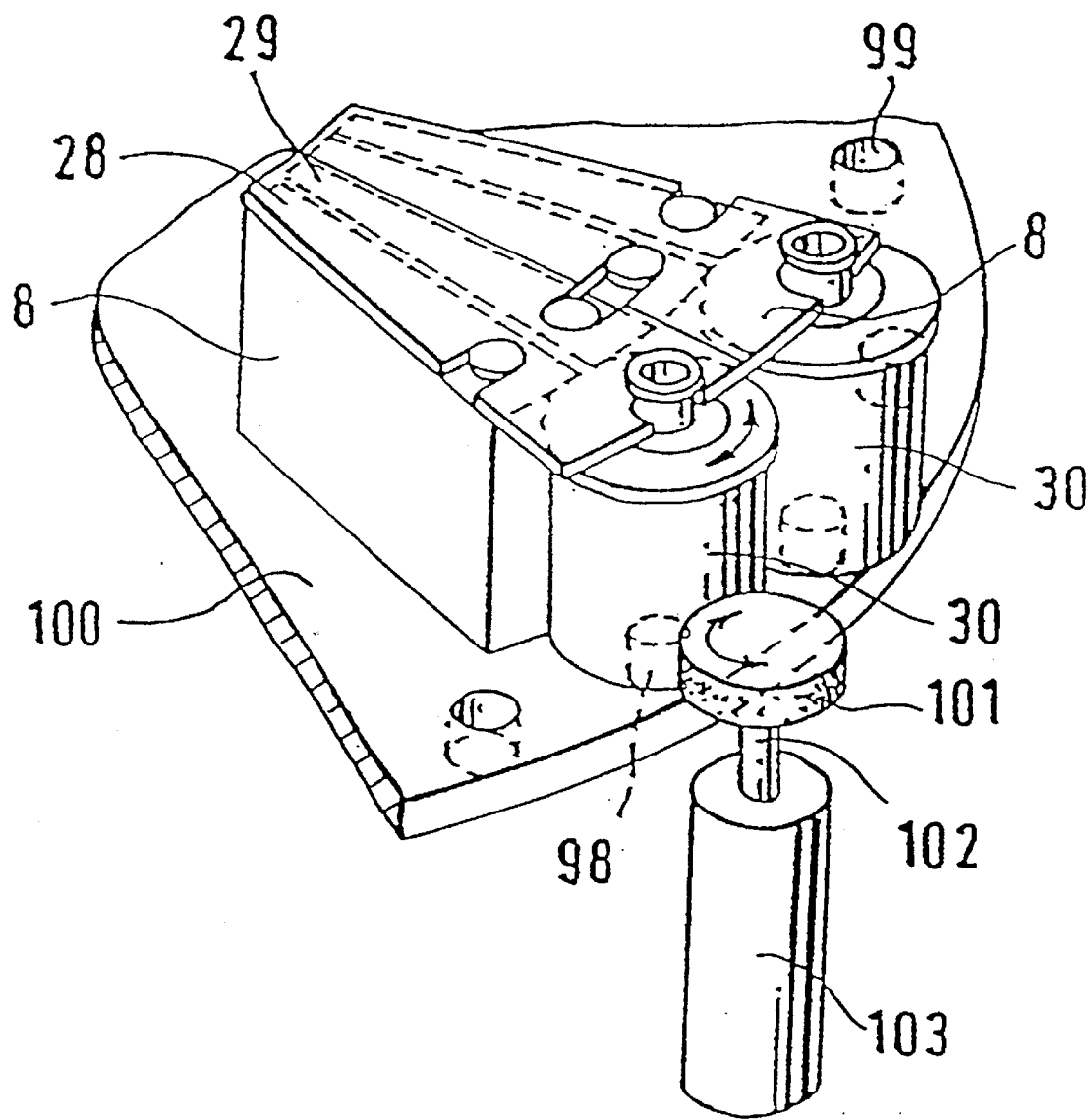
FIG. 3 shows a section of a reagent storage module in accordance with the present inventive concept.

Reagent/Sample Carousel (FIG. 1, FIG. 2 & FIG. 3)

The sample carousel (2) and reagent carousel (3) are concentric, the reagent carousel being the inner one. It is separated from the sampler carousel by a concentric ring carrying thermal insulation (5). The reagent carousel is cooled to 4° C.±2° C. Cooling is achieved using 6 five Watt Peltier cooling devices fitted to the underside of the carousel housing. Each of these carries a heat sink over which air is blown by six individual fans. The combined hot air is exhausted from the system via a common duct. As ambient air passes over the cooled metal underside of the reagent carousel, the floor of the unit is so designed that any water condensing on the cooled metal is collected in a trough and continuously sucked into system waste container (39).

The reagents are placed into their carousel in segment-shaped reagent packs (8) made up of three containers. A segment is divided down the middle into two equal segments (28 & 29) to form two of these containers, while the third is a cylindrical container (30) mounted on the outer circumference formed by the two segments. The bottom axle (98) of the container fits in a corresponding dry bearing (99) in the base (100) of the reagent carousel. This last vessel contains the magnetic solid phase suspension and is spun by a rubber wheel (101) attached to the shaft (102) Of a motor (103) mounted on the ring (5) separating the carousels. The position of the motor is such that a friction drive is established between the solid phase container and the rubber wheel.

In an alternative method the solid phase container (30) has an integral gear wheel moulded into the lower part of its circumference. This gear meshes with a drive gear mounted in the carousel housing so that the container may be spun to resuspend the solid material prior to aspiration. In both methods of rotation, positive feed back is provided to the computer by either a Hall effect device or a reflective opto device to ensure that the solid phase is adequately spun before it is sampled. These two sensors are of the type supplied by RS Components Ltd.

Such independently spinning containers (30) are the subject of EP-A-0435481, the entire contents of which are incorporated herein by reference.

The sample carousel has 20 slots (7) arranged tangentially around it each of which carries a sample tube rack (6) that can carry up to 4 individual sample tubes in holes (13) provided. The sample tubes can only be loaded into a sample rack (6) when it has been transferred to the sample load/unload station (4) under control of the computer. The sample rack can accept a wide range of sample tube sizes, the diameter of the actual tube loaded will be detected by an electronic tube diameter sizer (120) and the size of the tube will be stored in the computer.

This information is required so that the sample probe (46) can track the liquid meniscus during the time that the sample is being aspirated, in order to minimize contamination of the outside of the probe with the sample. The sample load/unload station (4) is covered with a transparent hood, and racks can only be transported between the load/unload station and the sample carousel (2) when this safety hood is closed. The station has 4 LEDs (107) by means of which the computer can indicate to the operator in which well (13) the sample tube should be inserted. As each sample tube well is monitored by an optical sensor (106) the computer will not accept the sample tube unless it is added to the well indicated by the illuminated LED (107).

After a sample rack has been filled and the lid has been closed the sample rack carriage (112) is driven along the guide bar (108) by the worm drive (109) that is turned by the dc motor (110). The position of the rack can be determined by the computer by using the reference position slop opto (115) and the optical decoder (111) fitted to the motor (110) shaft. When the carriage has reached the correct position the solenoid (113) is switched on and the sample tube rack is gripped by the rack clamp (114). The sample tube rack can now be driven to the carousel and placed in a free slot (7) in the sample carousel (2).

The sample identification number can be transferred to the computer either using the computer keyboard or by scanning a barcode label attached to the tube. After this number has been accepted by the computer only a short time, typically 5 seconds, is allowed for the operator to insert the tube, thus minimizing the chance that the incorrect tube will be inserted. When it is necessary to perform a short form recalibration the calibrators are provided ready for use in a plastic pack which consists of 4 separate plastic tubes joined together by a plastic strip across their mouths and carrying a special key (119) that activates a detector (118) in the tube rack to inform the computer that a recalibration is to be performed. These packs can contain one to four liquid calibrators that are provided in liquid form at the correct dilution for aspiration.

Figure 6A:
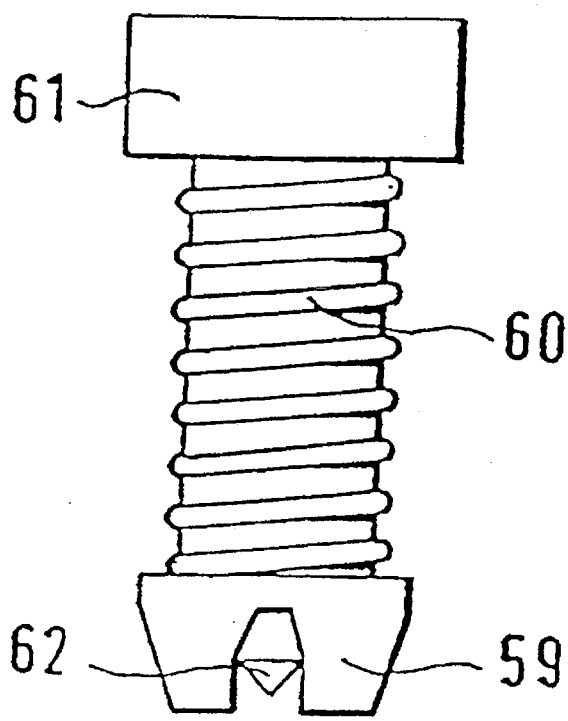
FIG. 6 shows a pick-up/pick-down apparatus, especially adapted for use with reaction cuvettes, and which conform part of a transport module in accordance with the present invention.
Figure 6B:
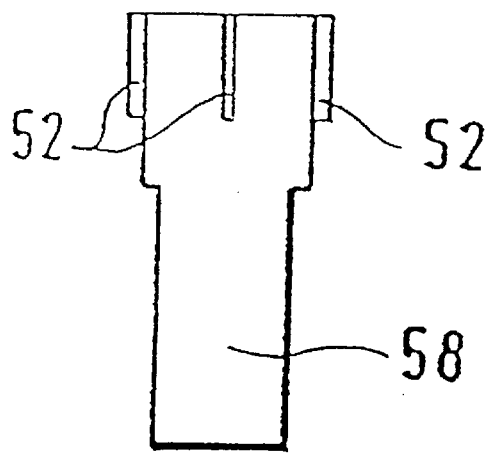
Figure 6C:
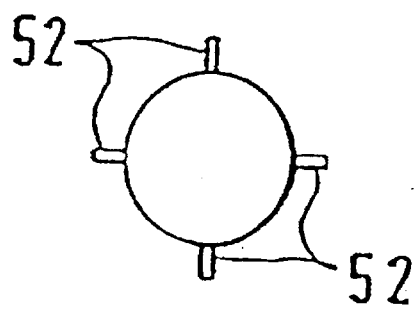
Figure 7A:
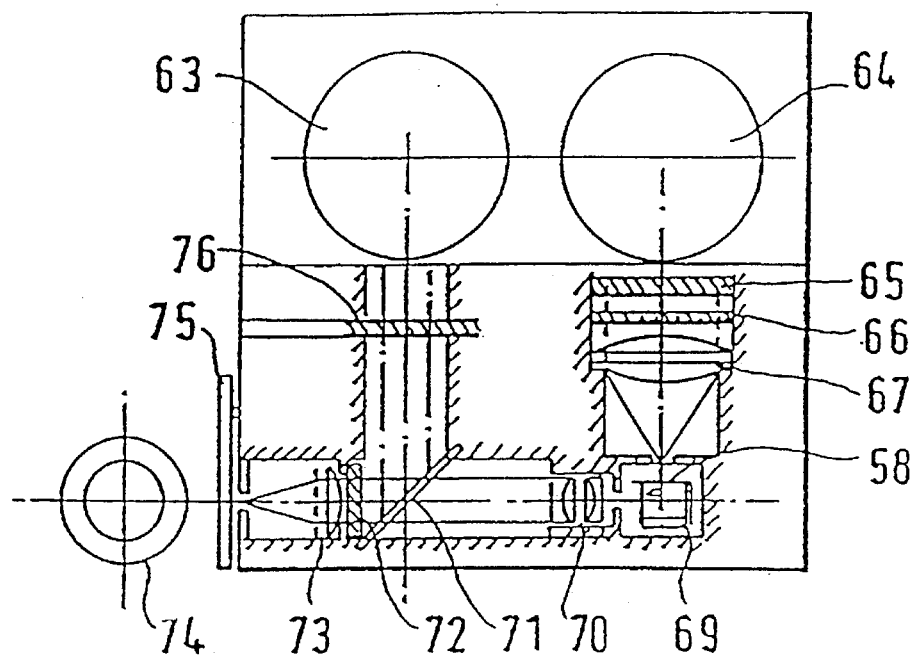
FIG. 7 shows a fluorimeter module in accordance with the present inventive concept.
Figure 7B:
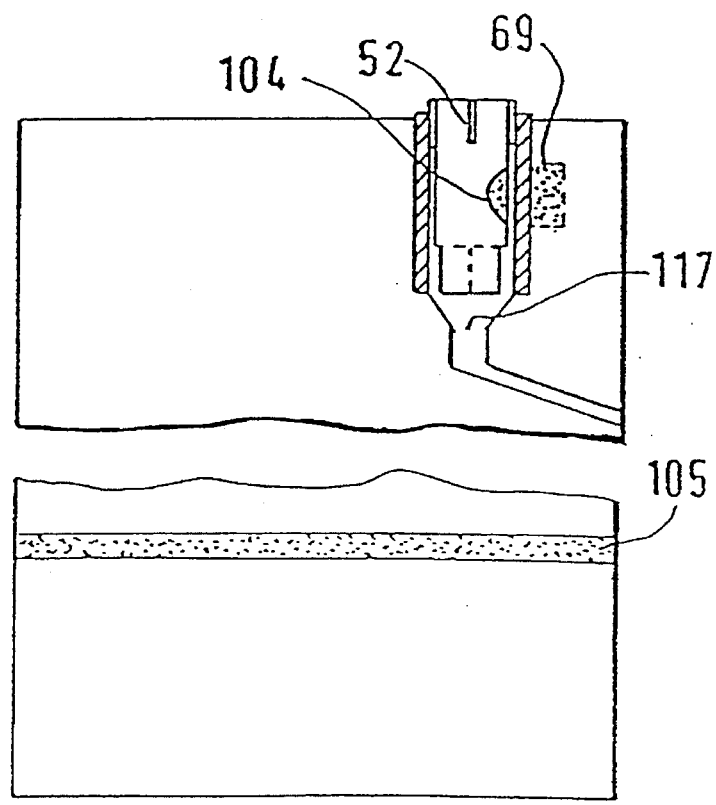
Figure 9:
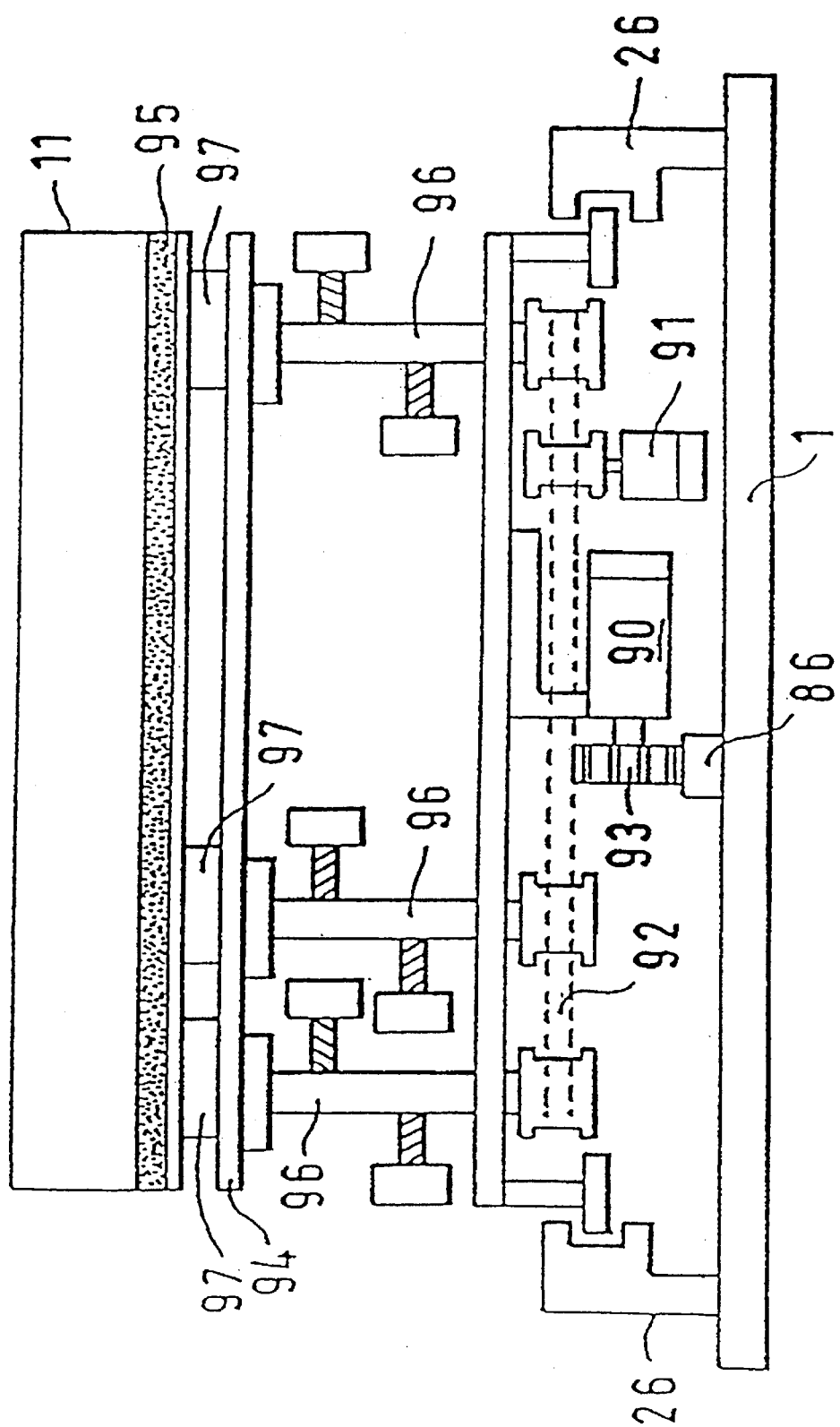
FIG. 9 shows a side view of an incubation module in accordance with the present inventive concept.

Incubator (FIG. 1, FIG. 6 & FIG. 9)

The incubator can carry a maximum of 224 cuvettes (58) that are contained in 4 separate 56-place cuvette holders (12). These holders are disposable and are supplied filled with cuvettes. The cuvette holders sit on a thermostated metal plate (11) that maintains a temperature of 37° C.±1° C. in the liquid contained in the cuvettes by means of an embedded heater mat (95) that is controlled via a thermistor and software servo loop. The metal plate is mounted on a carriage (94) that can be driven on two rails (26) in the z-direction across the instrument by means of a dc motor (90) drive by gear wheel (93) that meshes into a gear track (86) mounted on the chassis (1). The carriage is also capable of mixing the contents of the cuvettes by a gyratory mixing action. The dc motor (91) which powers this orbital movement is accurately accelerated, decelerated and positioned using an optical decoder on the dc motor shaft and a software servo loop. This is necessary in order to avoid splashing and to ensure that the grabber arm can accurately access the cuvettes after shaking. The orbital motion is created by driving three axles (96) by means of a belt (92) off the motor (91), these axles fit into bearings mounted off center in the three metal discs (97).

Figure 4:
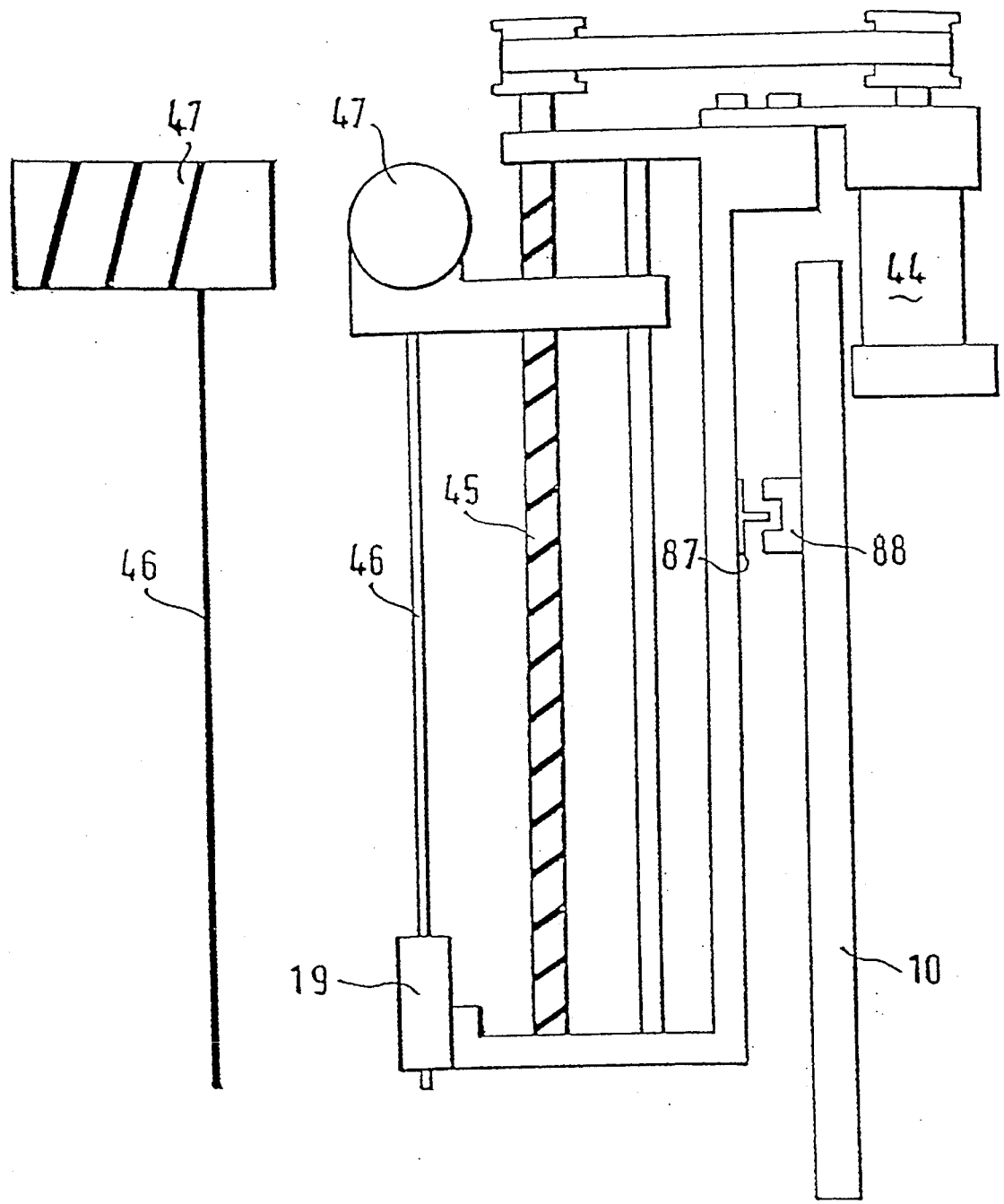
FIG. 4 shows that portion of a transport module in accordance with the present inventive concept which deals with fluid transport, and particularly illustrates a sample/reagent pipette mechanism for fluid transfer.

Sample/Reagent Probe (FIG. 1 & FIG. 4)

The sample/reagent probe is mounted on a carriage which can traverse the gantry in the x-direction. The carriage is propelled by a dc motor (31) which is controlled by a software servo loop using an optical encoder mounted on the shaft of the motor. The carriage also carries a small flag (87) which is used to trigger a reference slot opto (88) to enable the computer to establish a reference x-coordinate for the probe. A gear wheel (42) on the x-coordinate motor meshes in a gear track (43) mounted on the back wall of the gantry thus allowing the exact mechanical positioning of the probe.

The carriage has a second dc motor (44) which can move the probe up and down the y-axis on a screw drive (45). The upper position on the y-axis is fixed by a reference slot opto, the lower position is calculated by the computer depending on which container the probe (46) is accessing. The probe (46) permanently carries a transparent wash receptacle (19) with it enabling it to be washed as required while the probe is travelling along the x-axis. The outside of the probe is washed by injecting wash fluid into the wash receptacle on the left hand side and sucking it away on the right hand side using the system vacuum waste line. This means for probe decontamination is as used on instruments manufactured by Wilj International U.K., for example the SR1 system sold by Serono Diagnostics Limited.

The inside of the probe is washed by an air segmented wash liquid stream through the probe, this is sucked away by the same route as the external probe wash liquid.

When the probe accesses a sample or a reagent for the first time it uses its built in capacitive liquid level sense detector to detect the level of the liquid thus insuring that the probe only enters the liquid to a depth of approximately 1 mm. The computer stores information about the level of the liquid in the reagent containers and thus when the probe revisit the container it does not need to liquid level sense again. After the liquid has been measured into the probe it is sucked a further calculated distance so that the liquid is in the part of the probe which is coiled around a 25 watt heater block (47) thus allowing it to be heated to 37°±1 degrees C. The maximum temperature of this heater is controlled to 40 degrees C. in order to prevent thermal degradation of either samples or reagents. A modification of the above system consists of mounting two such probes on the same carriage. The advantage of the two probe system is that a longer time exists in each cycle for internal and external washing of the probe thus further reducing any possible carry over.

Gantry (FIG. 1)

The gantry (10) forms a heated pathway for the sample/reagent probe and the grabber arm. The back plate of the gantry (10) is heated and carries 3 fans (not shown) that insure that no thermal gradients build up across the gantry (10). The tubes carrying the wash liquids for the internal and external probe washes run the length of the gantry in good thermal contact with the back plate thus insuring that the wash liquid does not cool the probe during washing.

Figure 5A:
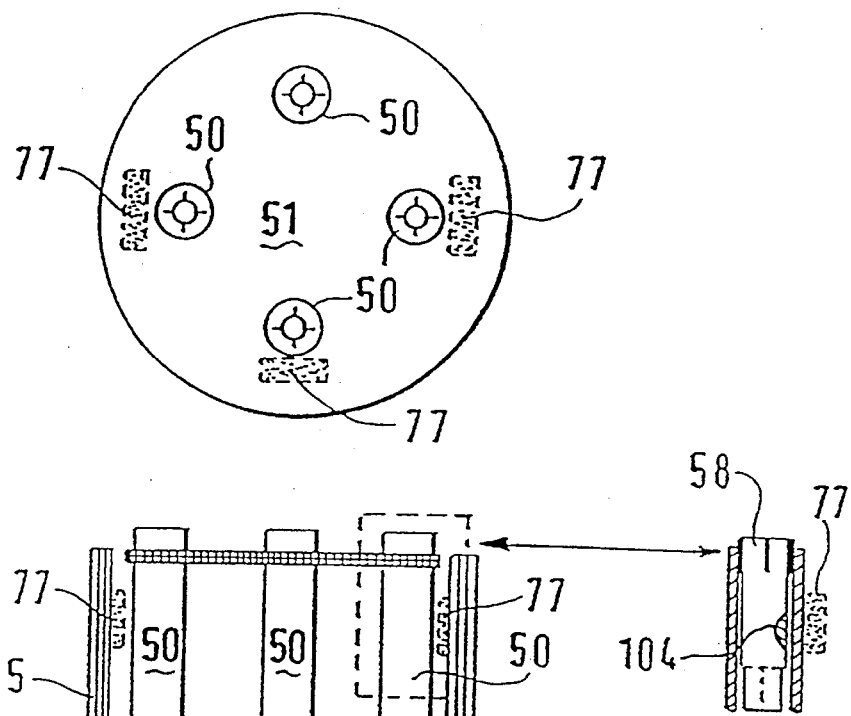
FIG. 5 shows a substrate and wash module in accordance with the present inventive concept.
Figure 5B:
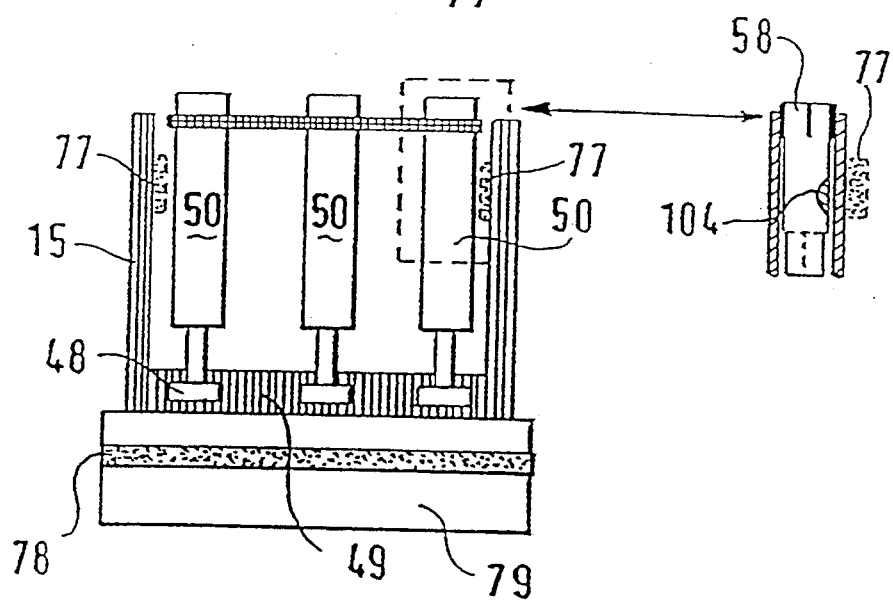
Figure 8A:
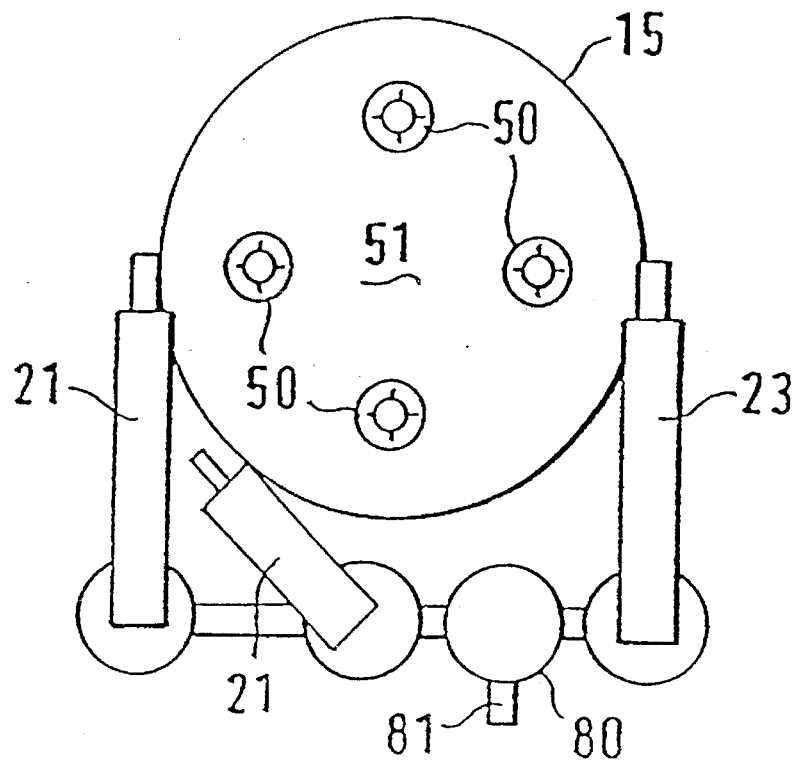
FIG. 8 shows additional detail of the substrate and wash module of FIG. 5, including various probes for aspirating and dispensing material to and from reaction curvettes mounted in the module.
Figure 8B:
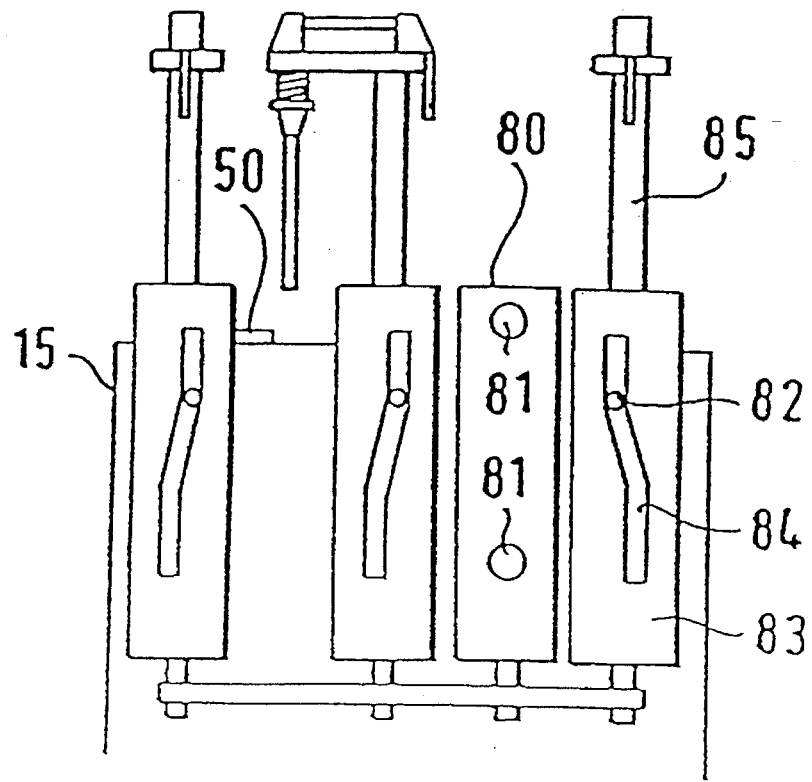

Substrate and Wash Station (SAW) (FIG. 1, FIG. 5 & FIG. 8)

The substrate and wash station (15) consists of a small carousel (51) around whose circumference four circular cuvette holders (50) are placed. The nature of the mounting of holders (50) in carousel (51) is immaterial provided holders (50) are independently rotatable; for example, carousel (51) can be designed with shaped recess portions corresponding to each holder (50) and provided with suitable bearings to permit rotation. The circumference of each cuvette holder carries a plastic gear (48) which meshes into a mating plastic gear (49) on the internal face of the SAW housing. Thus, when the carousel (51) rotates, the individual cuvette holders (50) rotate at a faster speed that the carousel in a type of planetary motion. Rotation of carousel (51) can be achieved by any known means, and such means is not critical. For example, a centrally located, vertically orientated driving shaft (not shown) can be positioned through carousel (51) and rotated by a motor (not shown) located at one end of the shaft. By repeatedly reversing the direction of travel of the SAW carousel (51) the resuspension of the solid phase in the cuvettes after magnetic separation is ensured. Apart from rotating freely to resuspend the solid phase as described above, the carousel cuvette positions are interchangeable by rotating through 90 degrees.

The cuvette position that is in line with the grabber arm is the pick up/put down station that allows the grabber arm to either transfer cuvettes into the SAW or out of it. The next two stations in an anti-clockwise direction round the SAW carousel are two identical wash stations. These two wash stations and the substrate addition station, a further 90° in the anti-clockwise direction have powerful permanent magnets (77) mounted close to the face of the cuvette to separate the magnetic solid phase (104) onto the wall of the cuvette before the aspirate cycle. Once the solid phase is pulled to the side the aspirate probes (21) are pulled down by the pneumatic cylinder (80) that is controlled by the air flow through the two control inlets/outlets (81). Each aspirate probe is rotated to the correct access position for the corresponding cuvette during this downward motion by a pin (82) that protrudes radially from the cylindrical rod (85) that carries the probe. This pin rides in a skewed slit (84) in the concentric tube (83) that surrounds the rod (85) carrying the pin (82). The vacuum system is switched through an electromagnetic valve to aspirate the contents of the cuvettes to waste. This method of operation ensures that the amount of residual liquid left in the cuvette is small and that no solid phase is lost. The aspirate probes are parked by switching the control air pressure to the pneumatic cylinder (80). Once the aspirate probes have been parked the dispense probes are moved into a position by a similar pneumatic control process.

The base (79) of the SAW station contains an embedded heater mat (78) which in conjunction with a thermistor and a software servo loop maintains a constant temperature within the SAW station. The tubing carrying the wash buffer and the substrate pass through this base to preheat the liquids before use. This heating is adequate for the wash buffer but the substrate is brought to 37° C.±0.2° C. by passing it through a heated dispense probe (23) to ensure that the enzymatic reaction commences at the correct temperature. The use of this arrangement allows the parallel processing of cuvettes during the separate and wash cycles.

Fluorimeter (FIG. 1, FIG. 5, FIG. 6 & FIG. 7)

The fluorimeter is a split beam system that uses a low pressure mercury lamp (74) as the light source. The amount of light energy at the required wave length of 365 nm is quite small but this is increased by the use of either a lamp integral or stand alone phosphor that converts the lower wave length energy to the required 365 nm. The light from the lamp can be shut off by activating the lamp shutter (75) positioned on the lamp housing. The light from the lamp passes through a collimator lens (73) and the required wavelength is selected by the use of a band pass filter (72). The emergent light passes through a lens system (70) that focuses the light on the cuvette (58) which is accurately positioned in the fluorimeter cuvette holder (32). Correct positioning is ensured by the four plastic wings (52) On the cuvette that mate into corresponding slits in the cuvette holder. In order to reduce the amount of stray light that enters the cuvette (58) the cuvette holder is covered by the cuvette shutter (68). This shutter is moved to the side to allow access for the grabber arm (20) to place a cuvette (58) in, or remove a cuvette from the cuvette holder. Two-slop optos (53), of the type available from RS Components Ltd, positively identify both the open and the closed position of the shutter. In order to prevent any damage in the case of a shutter failure the shutter is spring loaded to fail open.

The fluorimeter has its own dispense probe (24) to enable the addition of a stop solution for the enzymatic reaction should this be necessary. After the reading has been completed an aspirate probe (25) sucks the cuvette empty ready for return to its position within the incubator (11). The fluorescent light energy is measured at right angles to the incident beam and passes through a secondary high pass (66) and then a band pass filter (65) which for 4-methyl umbelliferone peaks at 450 nm. The light passing through these filters falls on the sample photomultiplier tube (64) and the signal is ratioed with the signal from the reference photomultiplier tube (63). The reference light for his pmt is obtained by splitting off a small portion of the primary beam using a beam splitter (71).

Before a measurement can be made the magnetic particles are separated onto the two faces of the cuvette that are not in the optical path. The magnet (69) collects the particles (104) at a height that is above the light path. This enables the measurement to be made in the presence of the solid phase without it having any influence on this measurement. This principle is an important part of the general inventive concept.

Underneath the cuvette a drain (117) is provided connected to the waste container (39) that is connected to the waste vacuum pump (40).

The fluorimeter has its own electronics that are operated under control of a dedicated micro processor. Stability of the fluorimeter is ensured by changing the pmt sensitivity by controlling the anode voltage using a software servo control loop. The reference light level for this control is obtained from two LEDs that are driven by constant current sources. The fluorimeter block has embedded in it a heating mantle (105) and a thermistor that allows a software servo loop to maintain the unit at 37° C.±1°.

Grabber Arm (FIG. 1 & FIG. 6)

The grabber arm (20) is mounted on a carriage which can traverse the gantry (10) in the x-direction. The carriage is propelled by a dc motor (54) which is controlled by a software servo loop using an optical encoder (55) mounted on the shaft of the motor. The carriage also carries a small flag which is used to trigger a reference slot opto (89) to enable the computer to establish a reference x-coordinate for the grabber arm (20). A gear wheel (56) on the x-coordinate motor meshes in a gear track (43) mounted on the back wall of the gantry (10) thus allowing the exact mechanical positioning of the grabber arm.

The carriage also has a second dc motor which can move the grabber arm up and down the y-axis on a screw drive (57). The upper position on the y-axis is fixed by a reference slop opto, the lower position is calculated by the computer depending on where the cuvette (58) to be moved is situated.

The grabber has 4 spring loaded fingers (59) that position themselves in the four segments of the circumference of the upper portion of the cuvette formed by the four plastic wings (52) which radiate from its outer circumference. These four fingers are held by a spring (60) in the gripping position. The strength of the grip can be adjusted by the tension adjustor (61) positioned above the retaining spring (60). A cuvette can only be released by compressing the spring (60) to open the fingers (59). To ensure that the cuvette drops from the grabber, a plunger (62) moves vertically down through the middle of the four open fingers during a cuvette deposition. An optical sensor positioned on the gantry detects whether or not the grabber is carrying a cuvette (58). Thus the computer can always check that the grabber has correctly collected or deposited a cuvette (58).

Pumps (FIG. 1)

Each pump (e.g., a Cavropump) consists of a precision glass cylinder fitted with a stepper motor driven plastic piston. These stepper motors are controlled by dedicated micro controllers that can be used to calibrate the delivery volumes exactly and optimize the rates of filling and exhausting the required volumes. The maximum retracted position of the pistons is detected by suitably placed optos. The system uses three cavros (34, 36, 38) for the single probe design and four for the two probe one. The operation of the syringe pumps can be seen on the SR1 instrument sold by Serono Diagnostics Limited.

Electronics (FIG. 1)

The system electronics may be contained in the hinged compartment (27) at the back of the instrument. The power supply unit is a switched mode one that obviates the necessity of using primary mains voltage range switching. The computer consists of two pc 20286 processor boards in a master slave combination that communicate with one another over a RS 232 link. The electronics for the probe liquid level sense is on a small pcb mounted on the probe assembly itself. The rest of the electronics for the system is mounted in the main electronics card cage.

Software

Obviously, software design is a user choice. However, a small part of the system software may be distributed in the various dedicated micro processors used in the following modules of the system:

1) The probe assembly liquid level sense.

2) The cavro controllers.

3) The fluorimeter.

The major part of the system software is used by the two pcs the system contains. The following is a list of the main functions that such software can perform:

1) The control of the user interface through the use of menus on the monitor screen and the combined light pen/barcode reader.
2) System status monitoring and reporting.
3) Resources management and reporting.
4) Storing and presenting QC data.
5) Scheduling of tests according to information given by the operator.
6) Storing and executing the protocols for each chemistry.
7) Storing and monitoring of calibration curves.
8) Updating of calibration curves after running calibrators.
9) Calculation and presentation of results.
10) Servo loop control for the various motors.
11) Enabling of intelligent testing and panel testing for specific functions.
12) Control of the internal and external printers.
13) Control of the system during a cold or warm start.
14) Error handling.
15) Fault handling and diagnosis.

Equivalents

Those skilled in the art will recognize or be able to ascertain using no more than routine experimentation, many equivalents to the specific embodiments of the invention described herein. Such equivalents are intended to be encompassed within the scope of this invention.

We claim:

1. An automated multi-test capability assay apparatus in modular form for non-sequential processing of samples for assay, comprising a reagent and/or assay sample storage module, an incubation module, a reaction detection/measurement module, transporting means for transporting reaction containers independently of each other between modules and for transferring reagents and/or assay samples between different modules without moving bulk reagents and/or assay samples intended for different tests, and computer control means for controlling said transporting means whereby at the time of loading samples said computer control means is programmable to direct a protocol of operations commensurate with said non-sequential processing of samples for assay for all said samples on load at said time in said apparatus independently of order of loading of said samples, and an apparatus for ensuring solid phase suspension comprising a housing, a rotatable support having means for independently rotatably mounting at least one vessel around a circumference of the support, the vessel having a vessel wall and containing assay or reaction components, a drive wheel for rotating the mounted vessel, and the housing including a driving surface on its internal face, the driving surface having a longer circumferential dimension than the drive wheel and surrounding the drive wheel and engageable therewith such that upon rotation of the rotatable support the drive wheel is rotated around the driving surface and the vessel thus rotated at a rate exceeding the rate of rotation of the rotatable support.

2. The assay apparatus of claim 1, wherein the rotatable support can rotate between a selected number of positions thereby to move a selected vessel containing assay or reaction components between those positions, fluid aspirating and/or dispensing means being provided adjacent at least one of those positions.

3. The assay apparatus of claim 1, wherein the apparatus for ensuring solid phase suspension includes magnet means positioned such that when a vessel containing assay or reaction components including a magnetizable solid phase material in the vessel is adjacent thereto the solid phase material is attracted and held to the vessel wall.

4. The assay apparatus of claim 1, wherein the drive wheel includes a gear wheel having teeth, the teeth of which engage a correspondingly toothed gear track which constitutes the driving surface.

5. The assay apparatus of claim 4, wherein the rotatable support and the drive wheel can be rotated in either direction to facilitate mixing of components in the vessel by alteration of rotational direction.

* * * * *